United States Patent [19]
Gutierrez et al.

[11] Patent Number: 5,334,775
[45] Date of Patent: Aug. 2, 1994

[54] POLYMER ALKYLATION OF HYDROXYAROMATIC COMPOUNDS

[75] Inventors: Antonio Gutierrez, Mercerville; Stuart L. Soled, Pittstown; Jose A. Paes, Scotch Plains, all of N.J.

[73] Assignee: Exxon Chemical Patents Inc., Linden, N.J.

[21] Appl. No.: 70,572

[22] Filed: Jun. 2, 1993

[51] Int. Cl.$^5$ .............................................. C07C 37/14
[52] U.S. Cl. ..................................... 568/791; 568/780; 568/790
[58] Field of Search ................ 568/780, 790, 791, 789

[56] References Cited

U.S. PATENT DOCUMENTS

| | | | |
|---|---|---|---|
| 3,346,657 | 10/1967 | Heake et al. | 260/671 |
| 3,711,406 | 1/1973 | Lowe | 252/33.4 |
| 3,795,615 | 3/1974 | Pappas et al. | 252/59 |
| 4,073,737 | 2/1978 | Elliott | 252/51.5 A |
| 4,108,945 | 8/1978 | Fetters et al. | 260/880 B |
| 4,234,435 | 11/1980 | Meinhardt et al. | 252/51.5 A |
| 4,283,573 | 8/1981 | Young | 568/794 |
| 4,323,714 | 4/1982 | Malloy et al. | 568/766 |
| 4,668,834 | 5/1987 | Rim et al. | 585/12 |
| 4,731,497 | 3/1988 | Grey | 585/455 |
| 4,735,582 | 4/1988 | Fusselman et al. | 439/329 |
| 4,839,070 | 6/1989 | Gutierrez et al. | 252/51.5 A |
| 4,849,569 | 7/1989 | Smith | 585/446 |
| 4,912,264 | 3/1990 | Masaki et al. | 568/790 |
| 4,952,739 | 8/1990 | Chen | 585/18 |
| 4,954,663 | 9/1990 | Marier et al. | 568/791 |
| 5,017,299 | 5/1991 | Gutierrez et al. | 252/51.5 R |
| 5,049,294 | 9/1991 | VanZon et al. | 252/51.5 A |
| 5,070,131 | 12/1991 | Rhodes et al. | 524/484 |
| 5,186,851 | 2/1993 | Gutierrez et al. | 252/49.006 |

FOREIGN PATENT DOCUMENTS

| | | |
|---|---|---|
| 128046 | 12/1984 | European Pat. Off. . |
| 129368 | 12/1984 | European Pat. Off. . |
| 387080 | 9/1990 | European Pat. Off. . |
| 400857 | 12/1990 | European Pat. Off. . |
| 440507A2 | 8/1991 | European Pat. Off. . |
| 462319A1 | 12/1991 | European Pat. Off. . |
| 2120953A | 12/1983 | United Kingdom . |

OTHER PUBLICATIONS

I. V. Kozhevnikov, A. I. Tsyganok, M. N. Timofeeva, S. M. Kulikov and V. N. Sidelnikov, "Alkylation of p-Substituted Phenols by Heteropoly Acids", React. Kinet, Catal. Lett., vol. 46, No. 1, 17–23.

T. Nishimura, T. Okuhara, and M. Misono, "High Catalytic Activities of Pseudoliquid Phase of Dodecatungstophosphoric Acid for Reactions of Polar Molecules", Chemistry Letters, pp. 1695–1698, 1991, The Chemical Society of Japan.

R. T. Sebulsky and Alfred M. Henke, "Alkylation of Benezene with Dodecene-1 Catalyzed by Supported Silicotungstic Acid", Ind. Eng. Chem. Process Des. Develop., Vol. 10, No. 2, 1971, pp. 272–279.

W. W. Yau, J. J. Kirkland and D. D. Bly, "Modern Size Exclusion Liquid Chromatography", John Wily & Sons, New York, 1979.

Primary Examiner—Werren B. Lone
Attorney, Agent, or Firm—H. L. Cohen

[57] ABSTRACT

A process for alkylating hydroxyaromatic compounds with a terminally unsaturated polymer in the presence of a partially or completely dehydrated heteropoly catalyst. The alkylated hydroxyaromatic compounds so formed are useful as precursors for the production of fuel and lubricant additives.

17 Claims, 1 Drawing Sheet

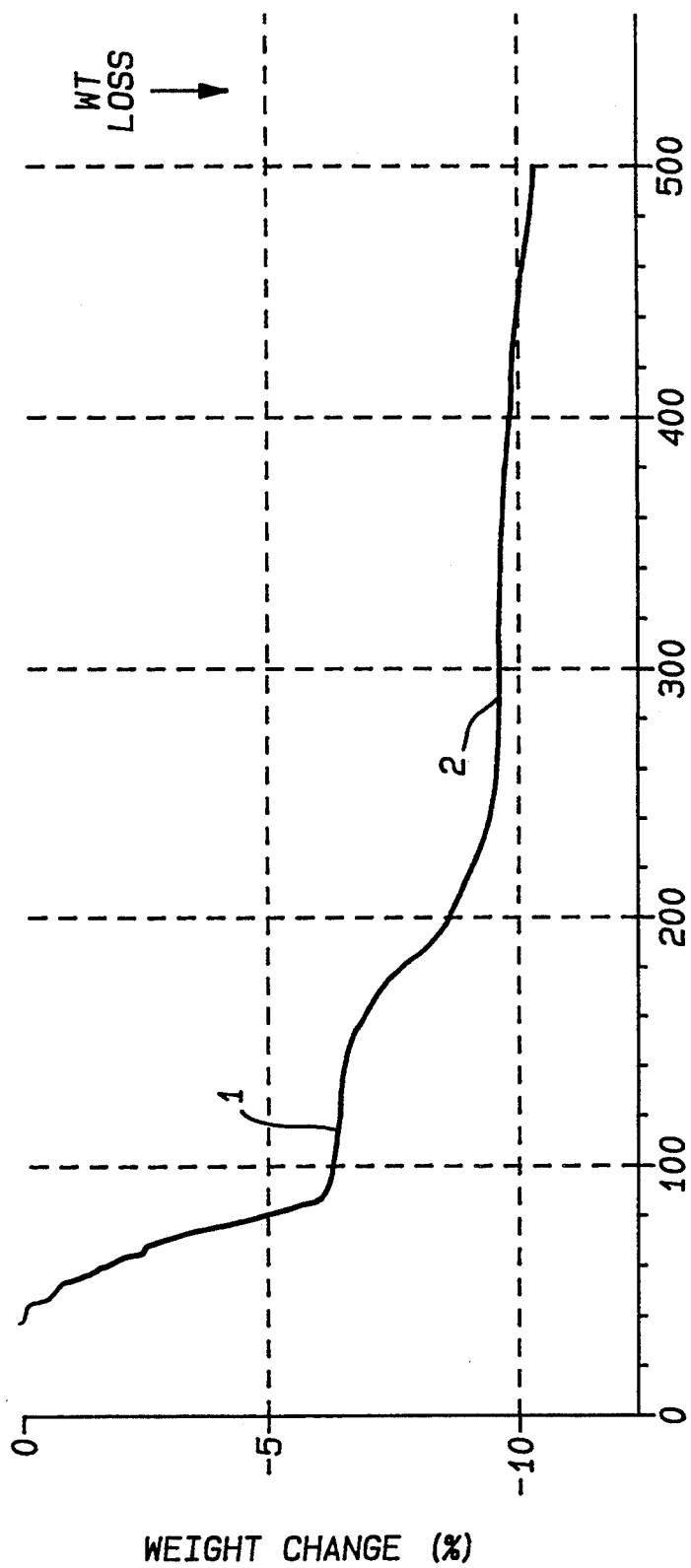

POLYMER ALKYLATION OF HYDROXYAROMATIC COMPOUNDS

The present invention relates to a novel process for producing hydroxy-functionalized polymers useful in the production of lubricant and fuel additives, such as dispersants and viscosity modifiers, by reacting an aromatic compound having at least one hydroxyl group with a long chain polymer olefin in the presence of a heteropoly catalyst.

BACKGROUND OF THE INVENTION

Various catalysts have been used to alkylate phenols with olefins. Traditionally, such alkylation reactions are carried out at atmospheric pressure with the reactants and catalyst in the liquid phase, referred to as "homogeneous catalysis", utilizing catalysts such as sulfuric acid, boron trifluoride, and aluminum chloride. Alkylation of phenols with olefins of up to 500,000 number average molecular weight have been disclosed, such as in U.S. Pat. No. 4,735,582, and EP Publication 440,507 A2. The drawback of homogeneous catalysis, of course, is the difficulty and expense in removing the catalyst from the liquid product.

In the attempt to find suitable solid (i.e. "heterogeneous") catalysts as an alternative to the traditional catalysts mentioned above, there have been proposed the use of more advanced catalysts in the last decade or so.

Zeolites have been described as useful in the alkylation of aromatics as described in U.S. Pat. Nos. 4,283,573; 4,731,497 and 4,954,663. The major drawback of zeolite catalysts, however, is that their catalytic activity is internal to their crystal structure. Hence, they are only effective upon reactants small enough to penetrate the pores of the zeolite crystal structure. Such catalysts are generally inefficient for any alkylating agent having more than 20 carbon atoms.

Mole sieves and exchange resins such as described in U.S. Pat. Nos. 4,323,714 and 4,849,569 and EP Publication 387,080 suffer similar problems to those of the aforementioned zeolites in that they are dependent upon the ability of the reactants to penetrate the resin structure. In general, these resins are less desirable than zeolites inasmuch as the relevant art teaches the use of alkylating agents of no more than 10 carbons in length. Amberlyst 15 has been utilized with success on alkylating agents having number average molecular weights in the thousands, but only at moderate rates of conversion.

Clays, layered materials and composites thereof are known such as described in UK Patent Application 2,120,953 and EP Application 400,857, but show no advantage over other catalysts insofar as the maximum size of the alkylation agent is concerned.

Directly relevant to the instant invention is U.S. Pat. No. 4,912,264 issued Mar. 27, 1990 to Sumitomo Chemical wherein alkylating agents comprising olefins having up to 13 carbon atoms are reacted with hydroxy-containing aromatics in the presence of a hydrated heteropoly acid and excess water. This patent indicates no or diminished yields for alkylating agents having more than 13 carbon atoms. Significantly, this method produces greater percentages of disubstituted product than monosubstituted. It is claimed that excess water is an advantage.

Also relevant is U.S. Pat. No. 3,346,657 issued Oct. 10, 1967, assigned to Gulf which refers to supporting a tungsten-based heteropoly acid upon a silica gel. High yields are obtained for dodecene-1 alkylation of benzene after calcination of the supported gel. The silica support is disclosed to be a major improvement over alumina supports.

Other disclosures of low molecular weight alkylations of aromatics in the presence of heteropoly catalysts are found in the scientific literature, such as T. Nishimura, T. Okuhara, and M. Misono, *Chemistry Letters*, p.1695 (1992) (alkylation of trimethyl benzene with cyclohexene and alkylation of phenol with 1-dodecene); R. Sebulsky and A.M. Henke, *Industrial and Engineering Chemistry. Process Design and Development*, Vol. 10, No. 2 (1971) (alkylation of benzene with 1-dodecene); and *Reaction Kinetics and Catalysis Letters*, Vol. 46, No. 1, p.17 (1992) (alkylation of p-tert-butyl phenol with hexene-1).

It is well known by those skilled in the art that as the molecular weight of the olefin used in an aromatic alkylation increases into the polymeric range, the alkylation becomes more difficult. Steric hindrance of the olefinic moiety and mass transfer limitations are recognized culprits. Increased acid strength improves yield, but is not always effective.

SUMMARY OF THE INVENTION

It has been found in the present invention that, upon significantly reducing the water content of certain heteropoly catalysts, it is now possible to alkylate hydroxy-containing aromatics with unsaturated polymers having number average molecular weights well over 1,000 at high yields and thereby enjoy the benefits of heterogeneous catalysis in the production of functionalized polymers useful as precursors in the production of fuel and lubricant additives such as dispersants and viscosity modifiers.

The use of heterogeneous catalysis allows for the continuous production of reaction products and is therefore useful for industrial mass production.

BRIEF DESCRIPTION OF THE DRAWING

FIG. 1 is a graph representation of one aspect of the invention.

DETAILED DESCRIPTION OF THE INVENTION

The process of the present invention results in the following catalyzed reaction:

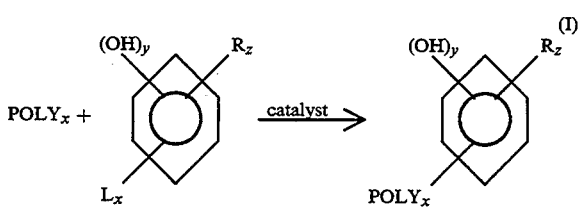

wherein $POLY_x$ represents x number of polymer alkylating agents, the same or different, $(OH)_y$ represents y number of hydroxyl groups, $R_z$ represents z number of substituents, the same or different, which may be hydrogen, hydrocarbyl, halide, aromatic or any other substituent that will not interfere with the progress of the reaction, and $L_x$ represents x number of leaving groups, which are usually hydrogen but may be tertiary hydrocarbyls, with the proviso that:

i) $x+y+z=6$, ii) X≧1, and
iii) y≧1.

The Hydroxyaromatics

Hydroxyaromatics useful in the present invention include, but are not limited to, the monohydric phenols such as phenol, o-, m-, or p-cresol, o-, m-, or p-ethylphenol, o-, m-, or p-isopropylphenol, o-, m-, or p-tert-butylphenol, o-, m-, or p-sec-butylphenol, 4-tert-butyl-6-methylphenol, 2,4-dimethylphenol, 2-methyl-4-ethylphenol, 2,4-diisopropylphenol, 4-methyl-6-iso-propylphenol, 2,6-di-tert-butylphenol, 2-tert-butyl-4-methylphenol, 3-methyl-6-tert-butylphenol, 2-chloro-4-methylphenol, p-chlorophenol, p-bromophenol, 2,4-dichlorophenol, 2,4-dibromophenol, 2-methyl-4-chlorophenol, 2-methyl-4-bromophenol, 2,4-dichloro-3-methylphenol, 3-methyl-6-cyclohexylphenol, 3-methyl-4-cyclohexylphenol, and so forth; the dihydroxyaromatics such as resorcinol, hydroquinone, catechol, 2-methylresorcinol, 2-chlororesorcinol, 2-carboxyresorcinol, 2-chlorohydroquinone, 4-tert-butylresorcinol, and so forth; the trihydroxyaromatics such as pyrogallol, phloroglucinol, 1,2,4-trihydroxybenzene, gallic acid and so forth; the naphthols such as alpha-naphthol, beta-naphthol, 2-hydroxy-3-carboxy naphthalene, 1-hydroxy-5-methyl naphthalene, 2-hydroxy-5-methyl naphthalene, 2-hydroxy-8-isopropyl-naphthalene, 2-hydroxy-5-isopropyl naphthalene, and so forth; and the anthranols and so forth.

Generally, all that is required of a hydroxyaromatic for the purposes of this invention is that there be at least one aromatic ring bound to a hydroxyl group and having at least one open carbon (e.g. bound to a hydrogen) at a position ortho or para thereto.

The Polymer Alkylating Agents

Polymer alkylating agents which are useful in the present invention are polyphers containing at least one carbon-carbon double bond (olefinic, or "ethylenic") unsaturation and which are not so sterically hindered, or in reactive competition with other functional groups, so as to render them unable to participate in the catalytic alkylation of the chosen hydroxyaromatic compound. As long as a chosen double bond will react in the presence of a chosen catalyst so as to alkylate a chosen hydroxyaromatic compound, such a bond will be deemed a "reactive" unsaturation and the polymer possessing such an unsaturation will be deemed a polymer alkylating agent.

Useful polymers in the present invention include polyalkenes including homopolymer, copolymer (used interchangeably with interpolymer) and mixtures thereof. Homopolymers and interpolymers include those derived from polymerizable olefin monomers of 2 to about 16 carbon atoms; usually 2 to about 6 carbon atoms. The interpolymers are those in which two or more olefin monomers are interpolymerized according to well-known conventional procedures to form polyalkenes having units within their structure derived from each of said two or more olefin monomers. Thus, "interpolymer(s)" as used herein is inclusive of terpolymers, tetrapolymers, and the like. As will be apparent to those of ordinary skill in the art, the polyalkenes from which the poly-substituent of Formula I are derived are often conventionally referred to as "polyolefin(s)".

Useful polymers include those described in U.S. Pat. Nos. 4,234,435, 5,017,299, 5,186,851 and European Patent No. 0,462,319-A1. Particular reference is made to the alpha-olefin polymers to be made using organometallic coordination compounds as disclosed therein. A particularly preferred class of polyphers are ethylene/alpha-olefin copolymers such as those disclosed in U.S. Pat. No. 5,017,299 and 5,186,851.

The active polymers for use in this invention possess at least one carbon-carbon unsaturated double bond. The unsaturation can be terminal, internal, or both. Preferred polymers have terminal unsaturation. The polymers of the present invention preferably comprise a high degree of terminal unsaturation. For the purposes of this invention, "terminal unsaturation" refers to the unsaturation provided by the last monomer unit located in the polymer. The unsaturation can be located anywhere in this terminal monomer unit. Terminal olefinic groups include ethenylidene (also known as "vinylidene") unsaturation, $R^aR^bC=CH_2$; trisubstituted olefin unsaturation, $R^aR^bC=CR^cH$; vinyl unsaturation, $R^aHC=CH_2$; 1,2-disubstituted terminal unsaturation, $R^aHC=CHR^b$; and tetra-substituted terminal unsaturation, $R^aR^bC=CR^cR^d$. At least one of $R^a$ and $R^b$ is a polymeric group, and the remainder are hydrocarbyl groups, polymeric or otherwise, the same or different.

The homopolymers and copolymers of the present invention can be conveniently characterized based on molecular weight range. Polymers and copolymers of "low", "intermediate" and "high" molecular weights can be prepared.

Low molecular weight polymers, also referred to herein as dispersant range molecular weight polymers, are considered to be polymers having a number average molecular weight of less than 20,000, preferably from about 500 to about 20,000 (e.g. 1,000 to 19,000), more preferably from about 1,500 to about 10,000 (e.g. 2,000 to 8,000) and most preferably from 1,500 to 5,000. The low molecular weights are number average molecular weights measured by vapor phase osmometry or gel permeation chromatography (GPC). Low molecular weight polymers are useful in forming dispersants for fuel and lubricant additives.

Medium molecular weight polymers, also referred to herein as viscosity modifier range molecular weight polymers, have number average molecular weights ranging from 20,000 to 200,000, preferably 25,000 to 100,000; and more preferably, from 25,000 to 80,000 and are useful for making viscosity index improvers for lubricating oil compositions, fuels, adhesive coatings, tackifiers and sealants. The medium number average molecular weights can be determined by membrane osmometry.

The high molecular weight materials have a number average molecular weights of greater than about 200,000 and can range from 201,000 to 15,000,000, and specific embodiment of 300,000 to 10,000,000 and more specifically 500,000 to 2,000,000. These polymers are useful in polymeric compositions and blends including elastomeric compositions. Higher molecular weight materials having number average molecular weights of from 20,000 to 15,000,000 can be measured by gel permeation chromatography with universal calibration, or by light scattering as recited in Billmeyer, Textbook of Polymer Science, Second Edition, pp.81–84 (1971).

The values of the ratio $\overline{M_w}/\overline{M_n}$, also referred to as molecular weight distribution, (MWD) are not critical. However, a typical minimum $\overline{M_w}/\overline{M_n}$ value of about 1.1 to 2.0 is preferred with typical ranges of about 1.1 up to about 4.

Useful olefin monomers from which the polyalkenes can be derived are polymerizable olefin monomers characterized by the presence of one or more unsaturated double bonds (i.e., >C=C<); that is, they are monoolefinic monomers such as ethylene, propylene, butene-1, isobutylene, and octene-1 or polyolefinic monomers (usually diolefinic monomers) such as butadiene-1,3 and isoprene.

These olefin monomers are preferably polymerizable terminal olefins; that is, olefins characterized by the presence in their structure of the group —R'—CH=CH$_2$, where R' is H or a hydrocarbyl group. However, polymerizable internal olefin monomers (sometimes referred to in the patent literature as medial olefins) characterized by the presence within their structure of the group:

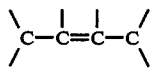

can also be used to form the polyalkenes. When internal olefin monomers are employed, they normally will be employed with terminal olefins to produce polyalkenes which are interpolymers. For purposes of this invention, when a particular polymerized olefin monomer can be classified as both a terminal olefin and an internal olefin, it will be deemed to be a terminal olefin. Thus, for example, pentadiene-1,3 (i.e., piperylene) is deemed to be a terminal olefin for purposes of this invention.

While the polyalkenes generally are hydrocarbon polyalkenes, they can contain substituted hydrocarbon groups such as lower alkoxy, lower alkyl mercapto, hydroxyl, mercapto, and carbonyl, provided the non-hydrocarbon moieties do not substantially interfere with the functionalization reactions of this invention. Preferably, such substituted hydrocarbon groups normally will not contribute more than about 10% by weight of the total weight of the polyalkenes. Since the polyalkene can contain such non-hydrocarbon substituent, it is apparent that the olefin monomers from which the polyalkenes are made can also contain such substituents. Normally, however, as a matter of practicality and expense, the olefin monomers and the polyalkenes will be free from non-hydrocarbon groups- (As used herein, the term "lower" when used with a chemical group such as in "lower alkyl" or "lower alkoxy" is intended to describe groups having up to seven carbon atoms.)

Although the polyalkenes may include aromatic groups (especially phenyl groups and lower alkyl- and-/or lower alkoxy-substituted phenyl groups such as para-(tert-butyl)phenyl) and cycloaliphatic groups such as would be obtained from polymerizable cyclic olefins or cycloaliphatic substituted-polymerizable acrylic olefins, the polyalkenes usually will be free from such groups. Again, because aromatic and cycloaliphatic groups can be present, the olefin monomers from which the polyalkenes are prepared can contain aromatic and cycloaliphatic groups.

There is a general preference for polyalkenes which are derived from the group consisting of homopolymers and interpolymers of terminal hydrocarbon olefins of 2 to about 16 carbon atoms. A more preferred class of polyalkenes are those selected from the group consisting of homopolymers and interpolymers of terminal olefins of 2 to about 6 carbon atoms, more preferably 2 to 4 carbon atoms.

Specific examples of terminal and internal olefin monomers which can be used to prepare the polyalkenes according to conventional, well-known polymerization techniques include ethylene; propylene; butene-1; butene-2; isobutylene; pentene-1; hexene-1; heptene-1; octene-1; nonene-1; decene-1; pentene-2; propylene-tetramer; diisobutylene; isobutylene trimer; butadiene-1,2; butadiene-1,3; pentadiene-1,2; pentadiene-1,3; pentadiene-1,3; isoprene; hexadiene-1,5; 2-chloro-butadiene-1,2; 2-methyl-heptene-1; 3-cyclohexylbutene-1; 2-methyl-5-propyl-hexene-1; pentene-3; octene-4; 3,3-dimethyl-pentene-1; styrene; 2,4-dichlorostyrene; divinylbenzene; vinyl acetate; allyl alcohol; 1-methyl-vinyl acetate; acrylonitrile; ethyl acrylate; methyl methacrylate; ethyl vinyl ether; and methyl vinyl ketone. Of these, the hydrocarbon polymerizable monomers are preferred and of these hydrocarbon monomers, the terminal olefin monomers are particularly preferred.

Useful polymers include alpha-olefin homopolymers and interpolymers, and ethylene/alpha-olefin copolymers and terpolymers. Specific examples of polyalkenes include polypropylene, polybutene, ethylene-propylene copolymer, ethylene-butene copolymer, propylene-butene copolymer, styrene-isobutylene copolymer, isobutylene-butadiene-1,3 copolymer, propene-isoprene copolymer, isobutylenechloroprene copolymer, isobutylene-(para-methyl)styrene copolymer, copolymer of hexene-1 with hexadiene-1,3, copolymer of octene-1, copolymer of 3,3-dimethyl-pentene-1 with hexene-1, and terpolymer of isobutylene, styrene and piperylene. More specific examples of such interpolymers include copolymer of 95% (by weight) of isobutylene with 5% (by weight) of styrene; terpolymer of 98% of isobutylene with 1% of piperylene and 1% of chloroprene; terpolymer of 95% of isobutylene with 2% of butene-1 and 3% of hexene-1; terpolymer of 60% of isobutylene with 20% of pentene-1; and 20% of octene-1; terpolymer of 90% of isobutylene with 2% of cyclohexene and 8% of propylene; and copolymer of 80% of ethylene and 20% of propylene.

A useful source of polyalkenes are the polybutylenes obtained by polymerization of C$_4$ refinery streams having a butene content of about 35 to about 75% by wt and an isobutylene content of about 30 to about 60% by wt in the presence of a Lewis acid catalyst such as aluminum trichloride or boron trifluoride.

It must be noted, however, that polyisobutylene contains quarternary carbon atoms in the polymer chain. Consequently, because the catalyst of the present invention is highly acidic, highly stable tertiary carbocations may form, thereby either cracking the polymer chain, migrating inward from the terminus of the chain and thereby shifting the location of the double bond, or some combination of both. Depending upon the strength of the acid, the residence time of the reaction, one may expect the $\overline{M}n$ of the polyisobutyl chains of the alkylated hydroxyaromatics to be substantially less than the $\overline{M}n$ of the polyisobutylene starting material and to find dimers, trimers and oligomers mixed in with the reaction product.

The degradation of quarternary carbon-containing polymer alkylating agents in the presence of strong acid catalyst is one reason why alpha-olefin homopolymers and interpolymers as well as ethylene/alpha-olefin copolymers and terpolymers are preferred.

Also useful are high molecular weight poly-n-butenes. Reference is made to commonly assigned copending U.S. Ser. No. 992,871, filed Dec.17, 1992 Docket No. PT-915entitled, "Amorphous Olefin Polymers, Copolymers, Methods of Preparation and Derivatives Thereof".

A preferred source of monomer for making poly-n-butenes is petroleum feedstreams such as Raffinate-2. These feedstocks are disclosed in the art such as in U.S. Pat. No. 4,952,739.

Preparing polyalkenes as described above which meet the various criteria for $\overline{M}n$ and $\overline{M}w/\overline{M}n$ is within the skill of the art and does not comprise part of the present invention.

Ethylene/Alpha-Alpha-Olefin Copolymer

The most preferred polymers suitable for use as alkylating agents are polymers of ethylene and at least one alpha-olefin, the alpha-olefin typically having the formula $H_2C=CHR^4$ wherein $R^4$ is straight chain or branched chain alkyl radical comprising 1 to 18 carbon atoms and wherein the polymer contains a high degree of terminal ethenylidene unsaturation. Preferably $R^4$ in the above formula is alkyl of from 1 to 8 carbon atoms and more preferably is alkyl of from 1 to 2 carbon atoms. Therefore, useful comonomers with ethylene in this invention include propylene, butene-1, hexene-1, octene-1, 4-methylpentene-1, decene-1, dodecene-1, tridecene-1, tetradecene-1, pentadecene-1, hexadecene-1, heptadecene-1, octadecene-1, nonadecene-1 and mixtures thereof (e.g. mixtures of propylene and butene-1, and the like). Preferred polymers are copolymers of ethylene and propylene and ethylene and butene-1.

The ethylene content of the polymers employed is preferably in the range of between about 20 and about 80%, and more preferably between about 30 and about 70% by mole. When butene-1 is employed as comonomer with ethylene, the ethylene content of such copolymer is most preferably between about 20 and about 45 weight %, although higher or lower ethylene contents may be present.

The most preferred ethylene-butene-1 copolymers are disclosed in commonly assigned U.S. Ser. No. 992,192, filed Dec. 17, 1992, titled POLYMERS DERIVED FROM ETHYLENE AND 1-BUTENE FOR USE IN THE PREPARATION OF LUBRICANT DISPERSANT ADDITIVES Docket No. PT-944 the disclosures of which are herein incorporated by reference.

The preferred method for making low molecular weight ethylene/α-olefin copolymer is described in commonly assigned U.S. Ser. No. 992,690, filed Dec.17, 1992, titled DILUTE PROCESS FOR THE POLYMERIZATION OF ETHYLENE/α-OLEFIN COPOLYMER USING METALLOCENE CATALYST SYSTEMS Docket No. PT-937, the disclosures of which are herein incorporated by reference.

The ethylene/alpha-olefin polymers generally possess a number average molecular weight as recited. Preferred ranges of molecular weights of polymer for use as precursors for dispersants of from about 500 to about 10,000, preferably of from about 1,000 to about 8,000, most preferably of from about 2,000 to about 6,000. The number average molecular weight for such polymers can be determined by several known techniques. A convenient method for such determination is by size exclusion chromatography (also known as gel permeation chromatography, or GPC) which additionally provides molecular weight distribution information, see W. W. Yau, J. J. Kirkland and D. D. Bly, "Modern Size Exclusion Liquid Chromatography", John Wiley and Sons, New York, 1979. Such polymers generally possess an intrinsic viscosity (as measured in tetralin at 135° C) of between about 0,025 and about 0.6 dl/g, preferably of between about 0.05 and about 0.5 dl/g, most preferably of between about 0,075 and about 0.4 dl/g. These polymers preferably exhibit a degree of crystallinity such that, when functionalized, they are oil soluble.

The preferred ethylene/alpha-olefin polymers are further characterized in that the polymer chains possess as much terminal ethenylidene- and ethenyl-type unsaturation as possible. Thus, one end of such polymers will be of the formula POLY'-$C(R'')=CH_2$ wherein $R''$ is $C_1$ to $C_{18}$ alkyl, preferably $C_1$ to $C_8$ alkyl, and more preferably $C_1$ to $C_2$ alkyl, (e.g., methyl or ethyl) and wherein POLY' represents the polymer chain; and a minor amount of the polymer chains may contain terminal ethenyl (i.e "vinyl") unsaturation, i.e. POLY'-$CH=CH_2$. The chain length of the $R''$ alkyl group will vary depending on the comonomer(s) selected for use in the polymerization. A portion of the polymers can contain internal monounsaturation, e.g. POLY'-$CH=CH(R'')$, wherein $R''$ is as defined above.

Good ethylene/alpha-olefin polymer comprises polymer chains, at least about 30% of which possess terminal ethenylidene unsaturation. Preferably at least about 50%, more -preferably at least about 60%, and most preferably at least about 75% (e.g. 75 to 98%), of such polymer chains exhibit terminal ethenylidene unsaturation. The percentage of polymer chains exhibiting terminal ethenylidene unsaturation may be determined by FTIR spectroscopic analysis, titration, HNMR, or $C_{13}NMR$.

The ethylene/alpha-olefin polymer and the compositions employed in this invention may be prepared as described in U.S. Pat. No. 4,668,834, in European Patent Publications 128,046 and 129,368, and in co-pending Ser. No. 728,111, filed Apr. 29, 1985, and copending Ser. No. 93,460, filed Sept. 10, 1987.

The polymers can be prepared by polymerizing monomer mixtures comprising ethylene in combination with other monomers such as alpha-olefins having from 20 carbon atoms (and preferably from 3 to 4 carbon atoms, i.e., propylene, butene-1, and mixtures thereof) in the presence of a metallocene catalyst system comprising at least one metallocene (e.g., a cyclopentadienyl-transition metal compound) and an activator, e.g. alumoxane compound. The comonomer content can be controlled through the selection of the metallocene catalyst component and by controlling the partial pressure of the various monomers.

The polymer for use in the present invention can include block and tapered copolymers derived from monomers comprising at least one conjugated diene with at least monovinyl aromatic monomer, preferably styrene. Useful polymers include polymers of the type disclosed in U.S. Pat. Nos. 4,073,737 and 3,795,615.

Such polymers should not be completely hydrogenated so that the polymeric composition contains terminal olefinic double bonds, preferably at least one bond per molecule. Useful polymers include an oil soluble copolymer of the following general formula:

$$(A)_x(B)_y \qquad (4)$$

wherein:
A is a conjugated diene of the formula:

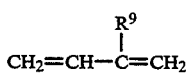

wherein $R^9$ is a H or $C_1$ to $C_8$ alkyl group, preferably H or $CH_3$ (i.e. isoprene) and present in mole % proportion as indicated by x which may vary from 45 to 99 mole %;

B is a $C_8$ to $C_{20}$ monovinyl aromatic compound and/or aromatic substituted diene and present in weight % proportion as indicated by y which may vary from 1 to 55 mole %; preferably 5 to 40 mole %, and optionally 25 to 30 mole % whereby the most useful composite properties of oxidative stability and $-18°$ C. viscosity of the lubricating oil blend is realized.

Block copolymers as used herein includes "multiple block copolymers" which term denotes copolymers consisting of two or more of the single block copolymers described above, which are bound to each other. A multiple block copolymer may, for example, be prepared by first copolymerizing to completion a mixture of butadiene and isoprene, thereafter polymerizing styrene onto said copolymer and subsequently sequentially copolymerizing a mixture of butadiene and isoprene followed by said styrene onto the "living" block copolymer. For purposes of this disclosure, a "living" copolymer is one which remains stable over an extended period of time during which additional monomers can be added to it.

Multiple block copolymers can also be obtained in other ways such as by coupling of two or more "living" block copolymer molecules. This can be achieved by addition of a compound which reacts with two or more "living" single block copolymer molecules. Examples of this type of compound include compounds containing two or more ester groups, compounds with more than one active halogen atom, e.g., di- and trichloromethyl-benzene, phosgene, dichloros i lane, carbon tetrachloride, dimethyldichlorosi lane, 1,2-dichloroethane, 1,2-dibromo-methane, and the like. Another possible method for preparing multiple block copolymers consists in the preparation of single block copolymer containing a reactive group in the molecule (e.g., a carboxyl group, which is, for example, obtained by bringing the polymerization of a single copolymer to an end by addition of carbon dioxide) and coupling of two or more of the molecules, e.g., by esterifying them with a di- or polyvalent alcohol. Multiple block copolymers have the further advantage that they can be tailored to provide the most useful additive properties while masking one or more undesirable properties inherent in any polymer block.

The present invention can also include star polymers as disclosed in patents such as U.S. Pat. Nos. 5,070,131; 4,108,945 and 3,711,406 as well as 5,049,294. Particularly useful star polymers are disclosed in U.S. Pat. No. 5,070,131.

The Catalyst

The present invention utilizes a heteropoly compound as the catalyst. A heteropoly catalyst may exist as the free acid (hereinafter "heteropoly acid") or salt (hereinafter "heteropoly salt") of a heteropolyanion.

Heteropolyanions are polymeric oxoanions formed by a condensation reaction of two or more different oxoanions, as by

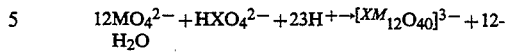

wherein M, known as the "poly-atom", is one or more Group VB or VIB transition metals (tungsten, molybdenum, vanadium, niobium, etc.) and X, known as the "hetero-atom", represents one or more Group IVB transition metals (titanium, zirconium, etc.) or the metalloids and non-transition metals of Group IIIA to VIIA (boron, aluminum, silicon, phosphorous, germanium, arsenic, tin, tellurium, etc.)

Primary Structure

The heteropolyanion takes the form of a so called "primary structure", perhaps the most well known being the Keggin ($\alpha$-type) structure wherein the metals M, are at the center of twelve $MO_6$ octahedra which surround a central $XO_4$ tetrahedron.

Other geometric isomers also exist, though the Keggin structure is the most common form. For example, $XM_{12}O_{42}$ (Siverton structure), $X_2M_{18}O_{62}$ (Dawson structure), $X_2M_5O_{23}$ (Strandberg structure), $XM_9O_{32}$ (unnamed), and $XM_6O_{24}$ (Linquist and Anderson structures) have also been produced, so it is to be understood that the primary structure of the catalyst of this invention is not limited to a particular polyanion composition or geometric isomer.

Useful heteropoly catalysts include the free acids (e.g., $H_3XM_{12}O_{40}$) phosphotungstic acid (also known as "12-tungstophosphoric acid" in the literature), borotungstic acid, titanotungstic acid, stannotungstic acid, phosphomolybdic acid, silicomolybdic acid, arsenomolybdic acid, teluromolybdic acid, aluminomolybdic acid, phosphovanadyltungstic acid (i.e. $H_4PW_{11}VO_{40}$), and the like, as well as the corresponding salts thereof.

The corresponding heteropoly salts may include monovalent, divalent, trivalent and tetravalent inorganic and/or organic cations such as, for example, sodium, copper, cesium, silver, ammonium, among others that have completely or partially ion-exchanged with the parent heteropoly acid (e.g., $Cs_3PW_{12}O_{40}$ or $Cs_2HPW_{12}O_{40}$ respectively). Hence, a heteropoly catalyst may exist as both a salt and an acid as, for example, $Cs_2HPW_{12}O_{40}$.

The free acid decomposes when heated to roughly $350°$ C. or above (the exact temperature varies with different acids), and the protons and a stoichiometric amount of the oxygen in the structure combine and are released as water vapor (still occasionally referred to as the "water of composition", now archaic since it is now known that the hydrogen and oxygen do not actually exist as water within the structure). Hence, for example, $H_3PW_{12}O_{40}$ releases 1.5 "waters of composition" while $CsH_2PW_{12}O_{40}$ releases only one upon decomposition.

Secondary Structure

Heteropoly catalysts in the solid state are composed of heteropolyanions, cations (protons and metal or onium ions), and water of crystallization. They may also contain neutral (or protonated) organic molecules (e.g. pyridine). Heteropolyanions are the primary structures while the 3-dimensional arrangements of the heteropolyanions with the cations and/or other components are referred to as the "secondary structures".

In secondary structures, primary structures are bridge-bonded to one another by cations, water, organics and/or combinations thereof- By way of example is $H_3PW_{12}O_{40} \cdot 6H_2O$ in which a pair of water molecules join with a proton to form an $H_5O_2^+$ structure

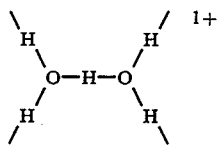

capable of bridging four $PW_{12}O_{40}^{3+}$ heteropolyanions. Alternatively the cesium ions $Cs^+$, in the salt $Cs_3PW_{12}O_{40}$ are presumed to serve the same function as $H_5O_2^{30}$.

As explained above, heteropoly catalysts may exist in the pure acid form (e.g. $H_3PW_{12}O_{40}$), the pure salt form (e.g. $Cs_3PW_{12}O_{40}$), and in forms containing both protons and metal cations (e.g. $Cs_2HPW_{12}O_{40}$) randomly distributed on sites interspersed between the heteropolyanions comprising the overall secondary structure. These latter proton/salt secondary structures may contain a wide range of compositions, as for example $Cs_{3-x}H_xPW_{12}O_{40}$ where $0 < - < 3$.

For the purposes of this invention, water combining with protons to form $H_5O_2^+$ cations (exclusive of the proton contribution of the waters of composition) are referred to as cation water. In the literature, cation water is alternatively referred to as water of hydration or water of crystallization. However, for the purposes of this invention, water of crystallization will only refer to water molecules in excess of cation water, while water of hydration will refer to both cation and excess water.

Referring to FIG. 1, it can be seen that the water of crystallization is weakly bonded to the secondary structure and is easily vaporized off at temperatures below 100° C. at atmospheric pressure, while cation water is hydrogen bonded into the secondary structure and requires temperatures in excess of 100° C. Cations derived from salts will generally not vaporize off at all.

The curve of FIG. 1 was obtained on a thermogravimetric analyzer wherein a 50 to 100 mg sample of phosphotungstic acid, $H_3PW_{12}O_{40} \cdot nH_2O$, was placed on a balance and subjected to a flow of dry air. The temperature of the air stream was increased 4° C. every minute, beginning at room temperature. A drop of about 6.2% weight to the first plateau, 1 (representing the loss of the water of crystallization), and 9.6% to the second, 2 (loss of cation water), suggests that the starting material averaged at least n=17 waters of hydration (i.e., at least 11 waters of crystallization) per heteropolyanion (20 waters of hydration would result in a 7.8% weight loss to the first plateau, 11.1% to the second—but the sample was observed to lose weight in the flowing dry air at room temperature such that some loss occurred before the balance was tared, so the exact value was not ascertained).

As a general rule, complete loss of the water of crystallization can be expected to occur at temperatures of up to about 120° C, while loss of the cation water may be expected to occur at temperatures from about 200° C. to 250° C., depending upon the heteropoly catalyst.

In FIG. 1, decomposition of the phosphotungstic sample can be seen to have occurred at about 350° C. as revealed by the release of the "water of composition", representing less than 1% of the weight of the original compound. A residue of $P_2O_5$ and $WO_3$ remained.

How much cation water and/or cation is incorporated into the secondary structure is believed to affect both the shape and acidity of the heteropoly catalyst. Changes in shape affect surface area. Surface area may be important in the present invention since most reactions of olefins with alkylaromatics are currently believed to occur on the surface of the catalyst rather than inside of it, though it is to be understood that this invention is not to be tied to any particular theory of heteropoly structure or mechanism.

In general, there may be no waters of hydration per heteropolyanion or as many as 32 waters of hydration per heteropolyanion. Most heteropoly acids of the Keggin type will have about 18 to 32 waters of hydration per heteropolyanion at room temperature (assuming 1 atmosphere and average humidity).

Most heteropoly salts can hold no more than about 3 cationic positive charges (e.g. 3 $Cs+$ or $H_5O_2^+$ cations or combination of both) per heteropolyanion, leaving room for about 24 additional waters of crystallization. It is now discovered that hydroxyaromatic compounds may be alkylated with polymer alkylating agents of substantial molecular weight by the use of heteropoly catalysts having substantially no water of crystallization.

Dehydration of the secondary structure is effected by baking the heteropoly catalyst in an oven, lyophilization, or heating under vacuum. Alternatively, saturated heteropoly catalyst may be used and the reaction carried out at or above the boiling point of water so as to drive water out of the catalyst and reaction mixture.

PREPARATION OF THE ALKYLATED HYDROXYAROMATIC COMPOUNDS

The selected polymer and hydroxyaromatic compound are contacted in the presence of a catalytically effective amount of at least one heteropoly catalyst under conditions effective to alkylate the aromatic group of the hydroxyaromatic compound.

The hydroxyaromatic compound and polymer will be typically contacted in a molar ratio of from 0.1 to 100, preferably from 1 to 50, more preferably from 2 to 20, moles of the aromatic compound per mole of the polymer. The selected acid catalyst can be employed in widely varying concentrations. Generally, the heteropoly catalyst will be charged to provide at least about 0.001, preferably from 0.01 to 0.9, more preferably from 0.05 to 0.4, moles of catalyst per mole of polymer alkylating agent charged to the alkylation reaction zone. Use of greater than 1 mole of the inorganic catalyst per mole of polymer alkylating agent is not generally required.

The temperature for alkylation can also vary widely, and will typically range from 20° to 250° C., preferably from 30° to 200° C., more preferably from 100° to 180° C. Temperatures over 100° C. are preferred to ensure that any water contamination is driven out of the reaction mixture. Note that if the catalyst is not calcined beforehand, then the reaction must be conducted above 100° C. in order to drive out the water of crystallization.

The reaction temperature will also affect the ratio of para-substituted to ortho-substituted reaction product. Reaction temperatures above 130° C. will favor nearly equal amounts of ortho- and para-substituted alkylated aromatic, anywhere from about 40 to 60% by weight of one to 60 to 40% by weight of the other. No disubstituted product was found at any of the temperatures tested. Reaction temperatures below 130° C. yield increasing proportions of para-substituted product. The actual temperature at which the transition occurs appears to depend upon the molecular weight and composition of the alkylating agent.

For industrial purposes a preferred temperature range is from about 150° C. to about 250° C. At these temperatures, the polymer alkylating agent is nicely liquid and easy to handle, and the reaction occurs rapidly. Of course, the exact temperature at which the polymer alkylating agent ceases to be "syrupy" depends upon the molecular weight and crystallinity of the polymer.

The alkylation reaction time can vary and will generally be from 0.5 to 5 hours, although longer or shorter times can also be employed. The alkylation process can be practiced in a batchwise, continuous or semicontinuous manner.

It should be noted that even polymers without quaternary carbons in their polymer chains are subject to a degree of double-bond migration as, for example:

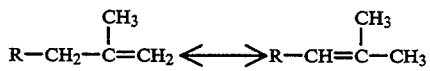

Hence, in batch reactions it may be desired that the hydroxyaromatic and the polymer be mixed before addition of the catalyst or, alternatively, that the hydroxyaromatic and catalyst be mixed first so as not to give the terminal unsaturations time to migrate. However, since the heteropoly catalysts are quite effective even with tetrasubstituted terminal unsaturations, the differences in yield are negligible.

The reaction may be carried out with or without a solvent. The solvents may be polar or non-polar with the proviso that they not be protic. Non-polar solvents are preferred since solvents of high enough polarity, even if non-protic, may cause partial or complete dissolution of the catalyst. Hence, preferred solvents include the aliphatic hydrocarbons, aromatic hydrocarbons, ethers, halogenated hydrocarbons, etc.

Preferred solvents are those sufficiently less volatile than water, under the reaction conditions utilized, so as to allow water to be driven out of the reaction mixture with minimal loss of solvent. Such solvents include the hydroxyaromatic reactants themselves as well as chlorinated aromatics such as the dichlorobenzenes (ortho, meta, and para), and hydrocarbons such as heptane, decane, and the like.

For mass production it is preferred that a continuous process be utilized. This involves continuously introducing reactants and solvents into a reaction zone and continuously drawing off the products of the reaction.

Means for either retaining the catalyst in the reaction zone are preferred, otherwise means for separating the catalyst from the product effluent and recycling it back to the reaction zone are required.

A simple means of retaining the catalyst in the reaction zone is to simply place a filter in a reaction vessel and draw the product stream out of the vessel through the filter.

If, however, it should be desired to recycle catalyst, such as in cases where a buildup of some contaminate occurs over time, then the catalyst may be separated from the vessel, the product output stream, or both by, for example, vortexing the solution so as to centrifugally extract the solid catalyst from the liquid medium that it may be drawn off for decontamination and later reintroduced into the reaction vessel in a continuous manner.

DERIVATIZATION OF THE FUNCTIONALIZED POLYMER

Dispersants maintain insoluble oxidation products in suspension in a lubricant or fuel, thereby preventing sludge flocculation and precipitation. Suitable dispersants include those of the ash-producing type (also known as detergent/inhibitors) and those of the ashless type, the latter being preferred.

The derivatized polymer compositions of the present invention can be used as ashless dispersants and multifunctional viscosity index improvers (MFVIs) in lubricant and fuel compositions. Ashless dispersants and MFVIs are referred to as being ashless despite the fact that, depending on their constitution, the dispersants may, upon combustion, yield a non-volatile material such as boric oxide or phosphorus pentoxide. The compounds useful as ashless dispersants generally are characterized by a polar group attached to a relatively high molecular weight hydrocarbon chain supplied by the functionalized polymer of the present invention. This polar group generally contains one or more of the elements nitrogen, oxygen, and phosphorus.

Processes for using alkylated hydroxyaromatics to make dispersants and viscosity modifiers are disclosed in U.S. application Ser. Nos. 473,582 (966,673) ALKYL-SUBSTITUTED HYDROXY-AROMATIC COMPOUNDS USEFUL AS A MULTI-FUNCTIONAL VISCOSITY INDEX IMPROVER, and 473,625, NOVEL ETHYLENE ALPHA-OLEFIN COPOLYMER SUBSTITUTED MANNICH BASE LUBRICANT DISPERSANT ADDITIVES, both filed on Jan. 2, 1990, commonly assigned to Exxon Chemical Patents, Inc., and hereby incorporated by reference.

EXAMPLES

The following examples are illustrative of the benefits of the present invention. Note that conversion figures are only accurate to within about 3 or 4 percentage points.

Also note that the conversion to active ingredient (alkylated phenol) is ascertained by purifying the reaction product mixture down to a mixture of unreacted polymer and alkylated phenol and measuring the weight % of active ingredient. However, this figure is not a exact measure of the mole conversion of polymer due to the added molecular weight of the phenol moiety. However, since the molecular weight of phenol is only 94, the difference is slight for high molecular weight polymers. A true molar conversion of polymer may be calculated as follows:

$$\text{Mole Conv.} = \frac{(\text{Mn poly} * AI)}{((\text{Mn poly} + 94) - 94 * AI)}$$

where AI indicates the weight fraction (i.e., wt%/100) of active ingredient in the purified sample (see columns 13 through 19 in Table 1), and $\overline{\text{Mn}}$ poly is the number average molecular weight of the polymer (column 2 in Table 1) and 94 is the molecular weight of phenol. The result of this equation is multiplied by 100 to derive the mole% conversion of starting polymer, which is reported in column 20 of Table 1.

PHENOL ALKYLATION EXAMPLES

Example 1

100 g of an EB (ethylene/butene) copolymer containing about 46% ethylene and 54% butene by mole with 37.8% ethenylidene double bond content and an average number molecular weight, $\overline{M}_n$, of 3300 was charged into four-neck round bottomed flask equipped with an air stirrer, thermometer, condenser, and nitrogen blanket. The polymer was mixed with 30 grams of phenol, 30 grams of o-dichlorobenzene and 10 grams of 12-tungstophosphoric acid ($H_3PW_{12}O_{40}$) obtained from Allan Chemicals, New York. The catalyst was calcined at 300° C. for one hour in a furnace prior to charging to the reaction vessel. The reaction mixture was then heated to 170° C. for 6 hours. A sample taken two hours into the reaction, after filtering and stripping, analyzed for 83.2% by weight of alkylated polymer. After six hours the reaction mixture was cooled down and diluted in one liter of heptane. The heptane slurry was filtered through a Celite 112 filter and stripped under vacuum at 200° C. until the weight ceased to drop. The final product, consisting of alkylated phenol and unreacted polymer, analyzed for 80% active ingredient (i.e. alkylated phenol) by weight. This demonstrates that the reaction was essentially complete after two hours.

NMR analysis of the active ingredient revealed a mixture of 55% ortho to 45% para monoalkylated isomers.

Example 2

About 100 grams of the copolymer of Example 1 was mixed with 30 grams of phenol, 30 grams of o-dichlorobenzene, and 10 grams of calcined 12-tungstophosphoric acid. The reaction was carried out in the same manner as in the procedure of Example 1, but at 150° C. The 2-hour sample analyzed for 83.3% active ingredient.

NMR analysis of the active ingredient revealed a mixture of 49% ortho to 51% para monoalkylated isomers.

Example 3

About 100 grams of the copolymer of Example 1 was mixed with 30 grams of phenol, 30 grams of o-dichlorobenzene, and 10 grams of calcined 12-tungstophosphoric acid at 300° C. for 1 hour. The reaction was carried out in the same manner as in the procedure of Example 1, but at 130° C. The two-hour sample analyzed for 84.1% active ingredient.

NMR analysis of the active ingredient revealed a mixture of 44% ortho to 56% para monoalkylated isomers.

Example 4

About 100 grams of the EB copolymer of Example 1 were mixed with 30 grams of phenol and 10 grams of 12-tungstophosphoric acid calcined at 300° C for 1 hour. reaction was carried out in the same manner as in Example 3, at 130° C. for 6 hours, but in the absence of o-dichlorobenzene as a solvent. The two hour sample analyzed for 78.9% active ingredient and the six-hour sample showed 79.8% active ingredient.

Example 5

About 100 grams of the copolymer of Example 1 was mixed with 30 grams of phenol, 30 grams of o-dichlorobenzene, and 10 grams of 12-tungstophosphoric acid. The reaction was carried out in the same manner as in Example 1, but at 100° C. The two-hour sample analyzed for 78.6% active ingredient and the final product at 6 hours analyzed for 78.6% active ingredient.

NMR analysis of the active ingredient revealed a mixture of 30% ortho to 70% para monoalkylated isomers.

Example 6

About 100 grams of the copolymer of Example 1 was mixed with 30 grams of phenol, 30 grams of o-dichlorobenzene, and 10 grams of 12-tungstophosphoric acid. The reaction was carried out in the same manner as in Example 1, but at 80° C. The two-hour sample analyzed for 79.8% active ingredient.

NMR analysis of the active ingredient revealed a mixture of 12% ortho to 88% para monoalkylated isomers.

Example 7

About 100 grams of the copolymer of Example 1 was mixed with 30 grams of phenol, 30 grams of o-dichlorobenzene, and 10 grams of 12-tungstophosphoric acid. The reaction was carried out in the same manner as in Example 1, but at 170° C. The two-hour sample analyzed for 83.3% active ingredient.

NMR analysis of the active ingredient revealed a mixture of 55% ortho to 45% para monoalkylated isomers.

Example 8

About 100 grams of the copolymer of Example 1 was mixed with 30 grams of phenol, 30 grams of o-dichlorobenzene, and 10 grams of 12-tungstophosphoric acid. The reaction was carried out in the same manner as in Example 1, but at 200° C. The two-hour sample analyzed for 80.0% active ingredient.

NMR analysis of the active ingredient revealed a mixture of 54% ortho to 46% para monoalkylated isomers.

Example 9

About 50 grams of an ethylene-butene copolymer containing 47.6% ethylene and 52.4% butene by mole with an average molecular weight of 3114 was charged into a reaction flask and mixed with 28 grams of phenol 5 grams of 12-tungstophosphoric acid calcined at 300° C. for 1 hour. The reaction mixture was heated to 175° C. under a nitrogen blanket and kept at this temperature for 6 hours while stirring. The product was diluted in heptane as in Example 1. The filtered product, free of unreacted phenol analyzed for 81.9% active ingredient at 2 hours, 80.8% at 4 hours and 78.4% at 6 hours.

Example 10

About 50 grams of the EB copolymer used in Example 9 were reacted with 14 grams of phenol in the presence of 5 grams of 12-tungstophosphoric acid calcined at 300° C. for 1 hour. The reaction mixture was heated at 175° C. for 6 hours while stirring under nitrogen blanket with the same procedure as Example 1. The filtered product, free of unreacted phenol analyzed for 78.2% active ingredient at 2 hours, 73.5% at 4 hours and 74.6% at 6 hours.

Example 11

Example 10 was repeated except that 0.5 of 12-tungstophosphoric acid were used. At the end of one hour at 175° C. a sample of the product analyzed for 72.2% active ingredient and at 6 hour for 76.3%.

Example 12

50 grams of the polymer of Example 9 were mixed with 7.9 grams of phenol and 50 grams of dichlorobenzene. About 15 grams 12-tungstophosphoric acid (vacuum oven dried at 100° C. for 5 hours) were added and the reaction mixture was then heated to 150° C. for six hours. After dilution, filtering, and stripping the final product analyzed for 85.1% active ingredient.

Example 13

50 grams of the polymer of Example 9 were mixed with 47.4 grams of phenol and 45 grams of 12-tungstophosphoric acid (vacuum dried, 5h 100° C.). Then the reaction mixture was heated to 150° C. for 6 hours in the absence of o-dichlorobenzene. After diluting in heptane, filtering, and stripping, the final product analyzed for 83.0% active ingredient.

Example 14

The reaction of Example 13 was repeated in exact manner except that 50 grams of o-dichlorobenzene were used. The final product analyzed for 84.4% active ingredient.

Example 15

2100 g of an ethylene-butene copolymer containing 31.3% ethylene by mole and 47.3% ethenylidene double bond with an average molecular weight of 4710 were charged into a reactor flask and mixed with 300 g phenol and 500 grams of o-dichlorobenzene. While mixing with an air stirrer 430 gram of 12-tungstophosphoric acid previously calcined at 300° C. for one hour were added. The reaction mixture was then heated to 175° C. for 6 hours. The slurry containing alkylated phenol, unreacted phenol, acid catalyst, and unreacted copolymer in dichlorobenzene was diluted in three separate flasks containing about one liter of heptane. The filtered samples, stripped of free unreacted phenol and solvent, analyzed as follows for active ingredient of alkylated phenol, the remaining being unreacted copolymer: 1 hour, 77.2%; 2 hours, 78.1%; 4 hours, 77.4%; 6 hours, 80.0%.

Example 16

4208 grams of an ethylene-butene copolymer containing 30% ethylene by mole and a ethenylidene double bond content of 48.2% with an average molecular weight of 3255 were charged into a 12 liter reactor and mixed with 1000 gram of phenol and 1400 grams of o-dichlorobenzene. Thereafter 397 grams of 12-tungstophosphoric acid, calcined at 300° C. for 1 hour, were added. While stirring with an air stirrer at about 500 rpm under nitrogen blanket, the reaction mixture was heated to 175° C. and soaked at this temperature for 4 hours. The product slurry was added to three flasks containing about one liter of heptane and filtered after allowed to settle for a couple of days. The final product, free of solvent and unreacted phenol, analyzed for 81.4% active ingredient.

Example 17

3500 grams of an ethylene-butene copolymer containing 47.9% ethylene by mole and a ethenylidene double bond content of 66.1% and having an average molecular weight of 3715 were charged to a 12 liter reactor and mixed with 1300 grams of o-dichlorobenzene, 700 grams of phenol and 400 grams of 12-tungstophosphoric acid calcined at 300° C. for one hour. The reaction mixture was then heated to 175° C. and soaked at this temperature for six hours. The final product was diluted in heptane as in Example 16, stripped and collected. It analyzed for a active ingredient of 85.5% of alkylated phenol.

Example 18

2,000 grams of the polymer of Example 17 were reacted with 400 grams of phenol, 170 grams of 12-tungstophosphoric acid (calcined at 300, 1 hr) and 750 grams of o-dichlorobenzene as in Example 17. The final product analyzed for 84.5% active ingredient.

Example 19

50 grams of the polymer used in Example 17 were reacted with 7.9 g of phenol, 50 g of o-dichlorobenzene and 15 grams of 12-tungstophosphoric acid using the same procedure as Example 17, except that the 12-tungstophosphoric acid was dried in a house vacuum oven at 100° C. for 5 hours. The final product analyzed for 77.6% active ingredient.

Example 20

50 grams of the polymer used in Example 17 were reacted with 14 grams of phenol, 35 grams o-dichlorobenzene, and 6.6 grams of 12-tungstophosphoric acid dried in a house vacuum oven at 100° C. for 5 hours. The final product analyzed for 85.6% active ingredient.

Example 21

100 grams of a ethylene-butene copolymer containing about 41.2% ethylene by mole with a ethenylidene double bond content of 37% and an average molecular weight of 2630 were mixed with 20 grams of phenol and 10 grams of 12-tungstophosphoric acid calcined at 300° C. for one hour. The reaction mixture was then heated to 175° C. for 6 hours while stirring under nitrogen blanket. The final product was diluted in one liter of heptane, filtered and stripped at 200° C. under high vacuum. It analyzed for 82.3% active ingredient.

Example 22

Exactly the same reaction as in Example 21 was repeated except that the reaction was carried out in the presence of 35 grams of ortho-dichlorobenzene. The product analyzed for 79.8% active ingredient.

Example 23

The same quantities and procedure of Example 22 were used except that the 12-tungstophosphoric acid was dried at 100° C. in a vacuum oven for one hour. The final product analyzed for 77.3% active ingredient.

Example 24

Example 23 was repeated except that 35 grams of ortho-dichlorobenzene were used. The final product analyzed for 77.5% active ingredient.

Example 25

2000 grams of an ethylene-butene copolymer containing 41.2% ethylene by mole, 37% ethenylidene double bonds and an average molecular weight of 2630 were mixed with 400 grams of phenol, and 400 grams of 12-tungstophosphoric acid (calcined at 300° C. for one hour). The reaction mixture was then heated to 150° C. while stirring under nitrogen blanket for a period of 10 hours. The mixture was then diluted in three separate flasks containing about one liter of heptane each. The heptane slurry was filtered thru a filter aid cake to removed the solid catalyst plus any crystallized phenol. The heptane solution was the vacuum distilled at 200° C. until constant weight. The final product analyzed for 82.5% active ingredient to active ingredient.

NMR analysis of the active ingredient revealed a mixture of 54% ortho to 46% para monoalkylated isomers.

Example 26

2000 grams of an ethylene-butene copolymer containing 47.3% ethylene by mole, 63% ethenylidene double bonds and an average molecular weight of 2182 were mixed with 400 grams of phenol and 400 grams of 12-tungstophosphoric acid (calcined at 300° C. for one hour). The reaction mixture was soaked at 150° C. for 6 hours and worked up as in Example 25. The final product analyzed for 91.4% active ingredient.

Example 27

2000 grams of the polymer of Example 26 were combined with 300 g of phenol and 300 grams of 12-tungstophosphoric acid (dried at 100° C. for 5 hours) and slowly heated to 150° C. Severe foaming occurred at 120–125° C.. A Dean Stark Trap was connected and the water that apparently was left in the 12-tungstophosphoric acid distill off at 130° C. for about one hour. After all the water distill off (about 12 cc), the reaction temperature slowly rose to 150° C. The reaction mixture was then heat soaked at 150° C. for 6 hours. More refluxing than usually was observed during this period. At the end of the sixth hour, the reaction product was diluted in heptane as in Example 26, filtered and stripped off solvent and unreacted phenol. It analyzed for an active ingredient of 74.6 with an ortho/para distribution of 23/77 respectively.

Example 28

50 grams of an ethylene-butene copolymer containing 66% ethenylidene double bonds and 54.2% ethylene by mole with a molecular weight of 1908 were mixed with 9 grams of phenol and 10 grams of 12-tungstophosphoric acid dried in a vacuum oven at 100° C. for 2 hours. The mixture was then heated to 150° C. for 10 hours. The work up sample analyzed for: 68% active ingredient at 2 hours, 79.2% at 6 hours, and 90.2% at the end of the 10 hours.

Example 29

Example 28 was repeated except that 55 grams of o-dichlorobenzene were used. The final product at 10 hours analyzed for 84.4% active ingredient.

Example 30

50 grams of an ethylene-butene copolymer containing 42% ethenylidene double bonds and an ethylene by mole content of 42% with an average molecular weight of 2275 were mixed with 7 grams of phenol, and 10 grams of 12-tungstophosphoric acid (calcined at 300° C., 1 hour). reaction mixture was then heated to 150° C. for 10 hours. The intermediate samples as well as the final mixture were diluted in heptane, filtered, and vacuum stripped at 200° C. until constant weight. The samples analyzed for: 78% active ingredient at 2 hours, 78.7% at 6 hours, and 77.6% at ten hours.

Example 31

Example 30 was repeated except that 20 grams of 12-tungstophosphoric acid were used. The sample analyzed for: 78.3% active ingredient at 2 hours, 76.6% at 6 hours, and 76.7% at ten hours.

Example 32

50 grams of an ethylene-butene copolymer containing 49.1% ethylene by mole, a ethenylidene double bond content of 63% an average molecular weight of 2076 were mixed with 10 grams of phenol and 10 grams of 12-tungstophosphoric acid (vacuum oven dried at 100° C. for one hour). The reaction mixture was then heated to 150° C. for 6 hours. After dilution in heptane, filtration, and stripping at 200° C. under vacuum the final product analyzed for 87.3% active ingredient.

Example 33

50 grams of an ethylene-butene copolymer containing 58.4% ethylene by mole, 60% ethenylidene double bond and an average molecular weight of 1818 were mixed with 10 grams of phenol and 10 grams of 12-tungstophosphoric acid (vacuum oven dried at 100° C. for one hour). The reaction mixture was then heated to 150° C. for six hours. After dilution in heptane, filtering and stripping at 200° C. under high vacuum until constant weight the final product analyzed for 87.0% active ingredient.

POLYMERS OTHER THAN EB

Example 34

200 grams of polynormalbutene (PNB, i.e., polybutene-1) with an average molecular weight of 550 were mixed with 102 grams of phenol and 40 grams of 12-tungstophosphoric acid (calcined at 300° C. for one hour). The reaction mixture was then heated to 150° C. for ten hours. The final mixture was then diluted in one liter of heptane, filtered and vacuum stripped at 180° C. until no further weight loss was observed.

NMR analysis of the active ingredient revealed a mixture of 29% ortho to 71% para monoalkylated isomers.

Example 35

50 grams of an ethylene-propylene copolymer obtained from Uniroyal containing 100% ethenylidene double bond and with an average molecular weight of 800 were charged into a reaction flask, mixed with 29 grams of phenol, and 10 grams of 12-tungstophosphoric acid (calcined at 300° C. for one hour). The reaction mixture was then heated to 150° C. for 10 hours. Intermediate samples and final product after dilution with heptane, filtered, and stripped analyzed for: 94.3% active ingredient at 2 hours, 93.7% at 6 hours, and 94.0% at 10 hours.

Example 36

100 grams of an ethylene-propylene copolymer containing 46% ethylene by mole and having an average molecular weight of 2000 were charged into a reaction flask and mixed with 15 grams of phenol and 10 grams of 12-tungstophosphoric acid (calcined at 300° C. for one hour). The reaction mixture was heated to 150° C. for 6 hours. The final product was diluted in on liter of heptane, filtered, and stripped under vacuum at 200° C. until constant weight. It analyzed for an active ingredient of 85.0%.

EXAMPLES USING SALTS OF 12-TUNGSTOPHOSPHORIC ACID

Example 37

20 grams of an EB copolymer containing 47.5% ethylene by mole, 47% ethenylidene double bond and an average MW of 2426 were charged into a reaction flask and mixed with 2.4 grams of phenol, 110 ml of chlorobenzene and 10 grams of a cesium salt of 12-tungstophosphoric acid, $Cs_{2.5}H_{0.5}PW_{12}O_{40}$ (hereinafter, CsHPA), vacuum dried at 110° C. for 6 hrs). The reaction mixture was then heated to 110° C. for a total period of 20 hours. Intermediate samples were taken and diluted in heptane, filtered and stripped at 200° C. under high vacuum. The samples analyzed for: 43.6% active ingredient at 6 hours and 58.5% at 20 hours.

Example 38

The same reaction as in Example 37 was repeated except that 50 ml of chlorobenzene were used and the reaction temperature was 136° C. The 20-hour sample showed 63.6% active ingredient.

Example 39

100 grams of the polymer of Example 37 were charged into a reaction flask and mixed with 14.1 grams of phenol and 20 grams of CsHPA(calcined at 300° C. 1 hr). The reaction mixture was then heated to 150° C. for 10 hours. The finished intermediate samples and the final product analyzed for: 73% active ingredient at 2 hours, 74.3 at 6 hours, and 76.1 at 10 hours

Example 40

The same reaction as Example 39 was repeated except that the cesium salt of 12-tungstophosphoric acid was not dried before reaction. The product analyzed for 79.6% active ingredient at 2 hours and 77.7% at 6 hours.

Example 41

100 grams of an ethylene-propylene copolymer of Example 30 were reacted with 15 grams of phenol and 20 grams of the cesium salt of 12-tungstophosphoric acid (dried at 300° C. 2 hrs) at 150° C. for 6 hours. After completion, the samples analyzed for: 85.5% active ingredient at 2 hours, and 80.0% at 6 hours.

Example 42

100 grams of the polymer of Example 37 were mixed with 14.1 grams of phenol and 20 grams of the ammonium salt of 12-tungstophosphoric acid, $(NH_4)_3PW_{12}O_{40}$, previously calcined at 300° C. for one hour. The reaction mixture was then heated at 150° C. for 10 hours. The sample were diluted in heptane, filtered and stripped at 200° C. under vacuum until constant weight. The intermediate samples and the final product analyzed for: 75.5% active ingredient at 2 hours, 79.9% at 6 hours, and 82.8% at 10 hours.

Example 43

50 grams of an EB copolymer containing 54.2% ethylene by mole, 66% ethenylidene double bond and an average molecular weight of 1,908 were charged into a reactor flask and mixed with 10 grams of phenol and 50 ml chlorobenzene, and 10 grams of $(NH_4)_3PW_{12}O_{40}$. The reaction mixture was the allowed to reflux for 10 hours at 130° C. The final product was diluted in heptane, filtered and stripped as before. It analyzed for 84.4% active ingredient.

Example 44

The reaction of Example 43 was repeated except that no solvent was used and the reaction temperature was kept at 150° C. for ten hours. The 2-hour sample showed 81.5% active ingredient, the 6-hour sample 80.8% active ingredient, and the final product analyzed for 85.5% active ingredient.

Example 45

100 gram of the polymer of Example 37 were reacted with phenol in the same manner as Example 37, but substituting o-dichlorobenzene for chlorobenzene and using 20 grams of the aluminum salt of 12-tungstophosphoric acid, $Al_{0.83}H_{0.5}PW_{12}O_{40}$. The sample analyzed for 73% active ingredient at 2 hours, 74.3% at 6 hours, and 76.1% at 10 hours.

The results of the above Examples are summarized in Table 1.

Surprisingly, no detectable amounts of disubstituted active ingredient appeared in those runs analyzed for ortho/para content. In the prior art of heteropoly alkylation, one generally expects to obtain at least about 5% disubstituted active ingredient.

TABLE 1

| Ex. No. 1 | Polymer/Cat 1 | Mn 2 | % C2 3 | % Ethenylidene 4 | Polymer g. 5 | Phenol g. 6 | Chlorobenzene g. 7 | o-diCl benzene g. 8 | Cat g. 9 | Calcine Temp. C. 10 | Calcine Time hrs. 11 |
|---|---|---|---|---|---|---|---|---|---|---|---|
| 1 | EB/W | 3300 | 46 | 37.8 | 100 | 30 | | 30 | 10 | 300 | 1 |
| 2 | EB/W | 3300 | 46 | 37.8 | 100 | 30 | | 30 | 10 | 300 | 1 |
| 3 | EB/W | 3300 | 46 | 37.8 | 100 | 30 | | 30 | 10 | 300 | 1 |
| 4 | EB/W | 3300 | 46 | 37.8 | 100 | 30 | | | 10 | 300 | 1 |
| 5 | EB/W | 3300 | 46 | 37.8 | 100 | 30 | 30 | | 10 | 300 | 1 |
| 6 | EB/W | 3300 | 46 | 37.8 | 100 | 30 | 30 | | 10 | 300 | 1 |
| 7 | EB/W | 3300 | 46 | 37.8 | 100 | 30 | 30 | | 10 | 300 | 1 |
| 8 | EB/W | 3300 | 46 | 37.8 | 100 | 30 | 30 | | 10 | 300 | 1 |
| 9 | EB/W | 3114 | 47.6 | | 50 | 28 | 30 | | 5 | 300 | 1 |
| 10 | EB/W | 3114 | 47.6 | | 50 | 14 | | | 5 | 300 | 1 |
| 11 | EB/W | 3114 | 47.6 | | 50 | 14 | | | 0.5 | 300 | 1 |

TABLE 1-continued

| | | | | | | | | | | | |
|---|---|---|---|---|---|---|---|---|---|---|---|
| 12 | EB/W | 3114 | 47.6 | | 50 | 7.9 | | 50 | 15 | 100 | 5 |
| 13 | EB/W | 3114 | 47.6 | | 50 | 47.4 | | | 45 | 100 | 5 |
| 14 | EB/W | 3114 | 47.6 | | 50 | 47.4 | | 50 | 45 | 100 | 5 |
| 15 | EB/W | 4710 | 31.3 | 47.3 | 2100 | 300 | | 500 | 430 | 300 | 1 |
| 16 | EB/W | 3255 | 30 | 48.2 | 4208 | 1000 | | 1400 | 397 | 300 | 1 |
| 17 | EB/W | 3715 | 47.9 | 66.1 | 3500 | 700 | | 1300 | 400 | 300 | 1 |
| 18 | EB/W | 3715 | 47.9 | 66.1 | 2000 | 400 | | 750 | 170 | 300 | 1 |
| 19 | EB/W | 3715 | 47.9 | 66.1 | 50 | 7.9 | | 50 | 15 | 100 | 5 |
| 20 | EB/W | 3715 | 47.9 | 66.1 | 50 | 14 | | 35 | 6.6 | 100 | 5 |
| 21 | EB/W | 2630 | 41.2 | 37 | 100 | 20 | | | 10 | 300 | 1 |
| 22 | EB/W | 2630 | 41.2 | 37 | 100 | 20 | | 35 | 10 | 300 | 1 |
| 23 | EB/W | 2630 | 41.2 | 37 | 100 | 20 | | 35 | 10 | 100 | 1 |
| 24 | EB/W | 2630 | 41.2 | 37 | 100 | 20 | | 35 | 10 | 100 | 1 |
| 25 | EB/W | 2630 | 41.2 | 37 | 2000 | 400 | | | 400 | 300 | 1 |
| 26 | EB/W | 2182 | 47.3 | 63 | 2000 | 400 | | | 400 | 300 | 1 |
| 27 | EB/W | 2182 | 47.3 | 63 | 2000 | 300 | | | 300 | 100 | 5 |
| 28 | EB/W | 1908 | 54.2 | 66 | 50 | 9 | | | 10 | 100 | 2 |
| 29 | EB/W | 1908 | 54.2 | 66 | 50 | 9 | | 55 | 10 | 100 | 2 |
| 30 | EB/W | 2275 | 42 | 42 | 50 | 7 | | | 10 | 300 | 1 |
| 31 | EB/W | 2275 | 42 | 42 | 50 | 7 | | | 20 | 300 | 1 |
| 32 | EB/W | 2076 | 49.1 | 63 | 50 | 10 | | | 10 | 100 | 1 |
| 33 | EB/W | 1818 | 58.4 | 60 | 50 | 10 | | | 10 | 100 | 1 |
| 34 | PNB/W | 550 | 0 | | 200 | 102 | | | 40 | 300 | 1 |
| 35 | EP/W | 800 | | 100 | 50 | 29 | | | 10 | 300 | 1 |
| 36 | EP/W | 2000 | 46 | | 100 | 15 | | | 10 | 300 | 1 |
| 37 | EB/C3 | 2426 | 47.5 | 47 | 20 | 2.4 | 110 | | 10 | 110 | 6 |
| 38 | EB/C3 | 2426 | 47.5 | 47 | 20 | 2.4 | 50 | | 10 | 110 | 6 |
| 39 | EB/C3 | 2426 | 47.5 | 47 | 20 | 14.1 | | | 20 | 300 | 1 |
| 40 | EB/C3 | 2426 | 47.5 | 47 | 20 | 14.1 | | | 20 | 20 | |
| 41 | EB/C3 | 2000 | 46 | | 100 | 15 | | | 20 | 300 | 2 |
| 42 | EB/NH4 | 2426 | 47.5 | 47 | 100 | 14.1 | | | 20 | 300 | 1 |
| 43 | EB/NH4 | 1908 | 54.2 | 66 | 50 | 10 | 50 | | 10 | 20 | |
| 44 | EB/NH4 | 1908 | 54.2 | 66 | 50 | 10 | | | 10 | 20 | |
| 45 | EB/A1 | 2426 | 47.5 | 47 | 100 | 2.4 | | 110 | 20 | 110 | 6 |

| Ex. No. | RX Temp C. 12 | % Al 1 hr 13 | % Al 2 hrs 14 | % Al 4 hrs 15 | % Al 6 hrs 16 | % Al 10 hrs 17 | % Al 20 hrs 18 | Final % Al 19 | Mole % Poly Conv. 20 | ortho % 21 | para % 22 |
|---|---|---|---|---|---|---|---|---|---|---|---|
| 1 | 170 | | 83.2 | | 80.0 | | | 80.0 | 79.5 | 55 | 45 |
| 2 | 150 | | 83.3 | | | | | 83.3 | 82.9 | 49 | 51 |
| 3 | 130 | | 84.1 | | | | | 84.1 | 83.7 | 44 | 56 |
| 4 | 130 | | 78.9 | | 79.8 | | | 79.8 | 79.3 | | |
| 5 | 100 | | 78.3 | | | | | 78.3 | 77.8 | 30 | 70 |
| 6 | 80 | | 79.8 | | | | | 79.8 | 79.3 | 12 | 88 |
| 7 | 170 | | 83.3 | | | | | 83.3 | 82.9 | 55 | 45 |
| 8 | 200 | | 80.0 | | | | | 80.0 | 79.5 | 54 | 46 |
| 9 | 175 | | 81.9 | 80.8 | 78.4 | | | 78.4 | 77.9 | | |
| 10 | 175 | | 78.2 | 73.5 | 74.6 | | | 74.6 | 74.0 | | |
| 11 | 175 | 72.2 | | | 76.3 | | | 76.3 | 75.8 | | |
| 12 | 150 | | | | 85.1 | | | 85.1 | 84.7 | | |
| 13 | 150 | | | | 83.0 | | | 83.0 | 82.6 | | |
| 14 | 150 | | | | 84.4 | | | 84.4 | 84.0 | | |
| 15 | 175 | 77.2 | 78.1 | 77.4 | 80.0 | | | 80.0 | 79.7 | | |
| 16 | 175 | | | 81.4 | | | | 81.4 | 81.0 | | |
| 17 | 175 | | | | 85.5 | | | 85.5 | 85.2 | | |
| 18 | 175 | | | | 84.5 | | | 84.5 | 84.2 | | |
| 19 | 175 | | | | 77.6 | | | 77.6 | 77.2 | | |
| 20 | 175 | | | | 85.6 | | | 85.6 | 85.3 | | |
| 21 | 175 | | | | 82.3 | | | 82.3 | 81.8 | | |
| 22 | 175 | | | | 79.8 | | | 79.8 | 79.2 | | |
| 23 | 175 | | | | 77.3 | | | 77.3 | 76.7 | | |
| 24 | 175 | | | | 77.5 | | | 77.5 | 76.9 | | |
| 25 | 150 | | | | | | 82.5 | 82.5 | 82.0 | 54 | 46 |
| 26 | 150 | | | | 91.4 | | | 91.4 | 91.1 | | |
| 27 | 150 | | | | 74.6 | | | 74.6 | 73.8 | 23 | 77 |
| 28 | 150 | | 68.0 | | 79.2 | 90.2 | | 90.2 | 89.8 | | |
| 29 | 150 | | | | | 84.4 | | 84.4 | 83.8 | | |
| 30 | 150 | | 78.0 | | 78.7 | 77.6 | | 77.6 | 76.9 | | |
| 31 | 150 | | 78.3 | | 76.6 | 76.7 | | 76.7 | 76.0 | | |
| 32 | 150 | | | | 87.3 | | | 87.3 | 86.8 | | |
| 33 | 150 | | | | 87.0 | | | 87.0 | 86.4 | | |
| 34 | 150 | | | | | 87.6 | | 87.6 | 85.8 | 29 | 71 |
| 35 | 150 | | 94.3 | | 93.7 | 94.0 | | 94.0 | 93.3 | | |
| 36 | 150 | | | | 85.0 | | | 85.0 | 84.4 | | |
| 37 | 110 | | | | 43.6 | | 58.5 | 58.5 | 57.6 | | |
| 38 | 136 | | | | | | 63.6 | 63.6 | 62.7 | | |
| 39 | 150 | | 73.0 | | 74.3 | 76.0 | | 76.0 | 75.3 | | |
| 40 | 150 | | 79.6 | | 77.7 | | | 77.7 | 77.0 | | |
| 41 | 150 | | 85.5 | | 80.0 | | | 80.0 | 79.3 | | |
| 42 | 150 | | 75.5 | | 79.9 | 82.8 | | 82.8 | 82.3 | | |
| 43 | 150 | | | | | 84.4 | | 84.4 | 83.8 | | |

TABLE 1-continued

| | | | | | | |
|---|---|---|---|---|---|---|
| 44 | 150 | 81.5 | 80.8 | 85.5 | 85.5 | 84.9 |
| 45 | 110 | 73.0 | 74.3 | 76.1 | 76.1 | 75.4 |

It also appears that the ratio of ortho-substituted active ingredient to para-substituted active ingredient approaches about 55%/45% at higher reaction temperatures (e.g., about 130° C. or higher), while low reaction temperatures generally result in a preponderance of para-substitution (about 20% ortho to 80% para at reaction temperatures below 100° C.).

In none of the samples subjected to NMR analysis did any detectable quantities of multisubstituted active ingredient appear.

COMPARATIVE EXAMPLES 100 grams of an ethylene-butene copolymer containing about 46% ethylene and 54% butene by mole with 37.8% ethenylidene double bond and an average number molecular weight, $\overline{M}n$, of 3600 were mixed with 30 grams of phenol, 35 grams of DCB, and 10 grams of 12-tungstophosphoric acid as specified in the following examples. The reaction mixture was held at 100° C. for 6 hours and a condenser was used to prevent any water from escaping the reaction vessel. Samples were taken at 2 and 6 hours.

EXAMPLE A

The 12-tungstophosphoric acid used in this reaction was used as it came in from the manufacturer without any drying at all, containing anywhere from 18 to 30 molecules of water per heteropolyanion. The sample analyzed for 6.8% active ingredient to alkyl phenol after 2 hours, 7.5% active ingredient after 6 hours.

EXAMPLE B

The 12-tungstophosphoric acid used in this example was dried in a vacuum oven at 90° C. for 1 hour. 10 grams of 12-tungstophosphoric acid lost 0.9 grams in weight. The 2-hour sample analyzed for 36.8% active ingredient and the 6-hour sample for 58.4%.

EXAMPLE C

The 12-tungstophosphoric acid was dried in a furnace at 300° C. for 1 hour. 1.5 grams of weight were lost for every 10 grams of 12-tungstophosphoric acid. The 2-hour sample analyzed for 78.6% active ingredient and the 6-hour sample for 79.1%.

EXAMPLES OF MANNICH BASE DISPERSANTS FROM ALKYLATED PHENOLS

The following Mannich Base Dispersants were prepared as follows:

The alkylated phenol (EB-Phenol), the diluent oil, and the corresponding polyamine were charged into a 500 ml four-neck round bottomed flask. The reaction mixture was then heated to 85° C. and formalin was slowly added over about one-half hour while stirring under nitrogen blanket. The reaction mixture was then soaked at this temperature for two hours. After two hours, the reaction temperature was slowly increased to 140–145° C. and kept at this temperature for an additional two hours. The solution was then borated by the addition of a slurry of boric acid in oil at 140° C. over a one-half hour period. The oil solution was soaked at 140° C. for two hours and stripped with a nitrogen stream for another hour. The product was then filtered and collected.

The following examples were prepared using the alkylated phenol obtained in Example 25. The final solution contained 30% active ingredient of functionalized polymer, the remainder bieng unreacted polymer and diluent oil.

TABLE 2

| Ex. No. | EB-Phenol | Poly-amine | Form-alin. | Dil. Oil | Boric Acid |
|---|---|---|---|---|---|
| 46 | 100 g | 3.6 g | 2.8 g | 112 g | 2.03 g |
| 47 | 70 g | 5.4 g | 2.8 g | 84 g | 3.00 g |
| 48 | 70 g | 3.6 g | 5.6 g | 84.5 g | 2.05 g |
| 49 | 70 g | 1.8 g | 8.4 g | 87.7 g | 1.02 g |
| 50 | 100 g | 1.8 g | 5.6 g | 113 g | 1.02 g |
| 51 | 90 g | 3.0 g | 4.7 g | 103.6 g | 1.7 g |
| 52 | 112 g | 2.3 g | 3.6 g | 123.8 g | 1.3 g |
| 53 | 100 g | 2.6 g | 4.2 g | 112.5 g | 1.5 g |

TABLE 3

| Amination-Boration Analytical Results | | | |
|---|---|---|---|
| Example | % Nitrogen | % Boron | Vis. 100° C. |
| 46 | 0.5 | 0.06 | 232 cs |
| 47 | 0.83 | 0.12 | 143 cs |
| 48 | 0.67 | 0.10 | 532 cs |
| 49 | 0.40 | 0.03 | 591 cs |
| 50 | 0.27 | 0.05 | 611 cs |
| 51 | 0.49 | 0.07 | 408 cs |
| 52 | 0.32 | 0.04 | 337 cs |
| 53 | 0.40 | 0.10 | 404 cs |

TABLE 4

| | SIB and VIB Test Results | |
|---|---|---|
| Example | SIB (mg sludge /10 g sludge) | VIB |
| 46 | 2.78 | 4 |
| 47 | 2.28 | 6 |
| 48 | 2.66 | 4 |
| 49 | 4.83 | 4 |
| 50 | 3.77 | 4 |
| 51 | 3.33 | 5 |
| 52 | 3.33 | 4 |
| PIBSA/PAM ref. | 4.16 | 5 |

Table 4 refers to Sludge Inhibition Bench tests (SIB) and Varnish Inhibition Bench tests (VIB) as compared to a conventional polyisobutylene succinic anhydride/-polyamine (PIBSA/PAM) dispersant reference.

The PIBSA/PAM reference is derived from a 2250 $\overline{M}n$ PIB functionalized with maleic anhydride and derivatized with a polyamine. This dispersant is representative of dispersants currently on the market. Test results of lower numerical value indicate superior performance.

The SIB and VIB tests forecast the performance of a lubricant composition in a gasoline engine. A detailed explanation of the tests is found in Gutierrez et al., U.S. Pat. No. 4,839,070, issued Jun. 13, 1989.

As can be seen, Mannich Base derivatives of the present invention generally demonstrate improved sludge and varnish inhibition over conventional PIBSA/PAM dispersants in gasoline engines.

Changes and modifications amounting to routine equivalents can be made by those skilled in the art to the embodiments as disclosed herein and such examples and illustrations as are disclosed are for explanatory purposes only and are not to be interpreted to limit the scope of the claims herein.

What is claimed is:

1. A process for producing an alkylated hydroxyaromatic compound, comprising:
   contacting, in the liquid phase,
   a hydroxyaromatic compound,
   a polymer alkylating agent of at least about 500 number average molecular weight and having at least one reactive carbon-carbon double bond unsaturation, and
   a heteropoly catalyst having substantially no waters of crystallization per heteropolyanion therein and forming an alkylated hydroxy aromatic compound.

2. A process according to claim 1, wherein said heteropoly catalyst is at least one member selected from the group consisting of phosphomolybdic acid, silicomolybdic acid, arsenomolybdic acid, telluromolybdic acid, aluminomolybdic acid, silicotungstic acid, phosphotungstic acid, borotungstic acid, titanotungstic acid, stannotungstic acid, and salts thereof.

3. A process according to claim 2, wherein said heteropoly catalyst is phosphotungstic acid.

4. A process according to claim 1, wherein said heteropoly catalyst has less than the maximum number of cation waters per heteropolyanion that its structure will permit.

5. A process according to claim 1, wherein said polymer alkylating agent is an unsaturated ethylene/alpha-olefin copolymer.

6. A process according to claim 5, wherein said alpha-olefin is propylene or butene-1.

7. A process according to claim 1, wherein said polymer alkylating agent is an alpha-olefin homopolymer or interpolymer.

8. A process according to claim 7, wherein said polymer alkylating agent is polybutene-1.

9. A process according to claim 1, wherein said heteropoly catalyst is separated from the reaction mixture for re-use.

10. A process according to claim 1, further comprising:
    continuously introducing said hydroxyaromatic compound and said alkylating agent into a reaction vessel; and
    continuously drawing the reaction product out from said reaction vessel; and
    means for preventing said heteropoly catalysts from being drawn out of said vessel with said reaction product.

11. A process according to claim 1, wherein the water content of said heteropoly catalyst is adjusted prior to the reaction by application of heat or vacuum or both to said catalyst.

12. A process according to claim 11, wherein the temperature to which said heteropoly catalyst is subjected is from 20° C. to 350° C.

13. A dispersant comprising a Mannich Base derivative of a reaction product of the process of claim 1.

14. A composition produced by the process of claim 1 wherein at least 90% of active ingredient produced is monoalkylated phenol.

15. The composition of claim 14, wherein:
    40% to 60% of said active ingredient is para-substituted alkylated hydroxyaromatic compound; and
    40% to 60% of said active ingredient is ortho-substituted alkylated hydroxyaromatic compound.

16. The composition of claim 15 wherein less than 10% of said active ingredient is multi-substituted alkylated phenol.

17. A dispersant composition comprising Mannich Base derivatives of the active ingredients of the composition of claim 14.

* * * * *